United States Patent
Lindenmeier et al.

[19]

[11] Patent Number: 5,868,739
[45] Date of Patent: Feb. 9, 1999

[54] SYSTEM FOR CUTTING BIOLOGICAL TISSUE

[75] Inventors: Heinz Lindenmeier, Planegg; Georg Lohr, Ottobrunn; Karl Fastenmeier, Munich; Gerhard Flachenecker, deceased, late of Ottobrunn, all of Germany, by Hilegard Flachenecker, legal representative

[73] Assignee: Karl Storz GmbH & Co., Tuttlingen, Germany

[21] Appl. No.: 555,254

[22] Filed: Nov. 8, 1995

Related U.S. Application Data

[63] Continuation of Ser. No. 193,111, filed as PCT/DE92/00675, Aug. 12, 1992, published as WO93/03680, Mar. 4, 1993, Jul. 18, 1994, abandoned.

[30] Foreign Application Priority Data

Aug. 12, 1991 [DE] Germany ............... 41 26 608.0

[51] Int. Cl.⁶ .................................................. A61B 17/36
[52] U.S. Cl. ................................. 606/39; 606/34
[58] Field of Search ..................... 606/32–34, 37–40

[56] References Cited

U.S. PATENT DOCUMENTS

| | | | |
|---|---|---|---|
| 4,209,018 | 6/1980 | Meinke et al. | 606/38 |
| 4,474,179 | 10/1984 | Koch | 606/40 |
| 4,860,745 | 8/1989 | Farin et al. | 606/40 |
| 5,108,391 | 4/1992 | Flachenecker | 606/40 |
| 5,133,711 | 7/1992 | Hagen | 606/40 |
| 5,167,658 | 12/1992 | Ensslin | 606/34 |
| 5,167,660 | 12/1992 | Altendorf | 606/46 |

*Primary Examiner*—Michael Peffley
*Attorney, Agent, or Firm*—Donald D. Mon; David O'Reilly

[57] ABSTRACT

A system for controlling the operation of a high frequency biological tissue cutting device for cutting biological tissue with high-frequency current having a HF generator component designed so that the amplitude of the voltage (UG) applied to the tissue can be changed. At least one adjustment device is provided to adjust one of the characteristic values (K) of the high frequency generator component to a 1st desired value (b), related to the output of an indicator device that indicates by an electrical signal (d) the size and intensity of the electric arc occurring between the surgical probe and the tissue during cutting. A desired-value transmitter provides a second desired value (c) representing the desired size and intensity of the electric arc. An evaluation unit receives the output signal (d) of the indicator device and the 2nd desired value representing the intensity of the electric arc (c) and provides therefrom a desired value (b) output for the adjustment device such that the maximum changing speed of the desired value (b) is at least one magnitude smaller than the speed with which the adjustment device adjusts the characteristic value (K) of the high-frequency generator component.

16 Claims, 6 Drawing Sheets

SYSTEM FOR CUTTING BIOLOGICAL TISSUE

This is a continuation of application Ser. No. 08/193,111, filed as PCT/DE92/00675 Aug. 2, 1992 published as WO93/03680 mar. 4, 1993, abandoned.

TECHNICAL FIELD

The present invention relates to a system for cutting biological tissue with high-frequency current.

STATE OF THE ART

High-frequency currents are employed in surgery to cut biological tissue or to coagulate, i.e. stop the bleeding. During cutting, an almost continuous high-frequency power is supplied. A problem in high-frequency surgery is the right dosage of the power during cutting. If the power is set too low, the tissue undergoes mechanical stress, it cannot be cut quickly or the cutting procedure comes to a complete halt. On the other hand, setting the high-frequency power too high results in a strong electric arc between the surgical probe and the tissue. This electric arc causes major tissue necrosis which impairs the healing process. Too strong an electric arc has also other drawbacks. The essential disadvantage is a partial rectification of the high-frequency current due to the electric arc, which leads to the danger of nerve and muscle stimulation in the patient. Such muscle and nerve stimulation may result in sudden, unexpected movements by the patient even if the patient is under full narcosis. In this event, the surgeon no longer has control, and there is high risk that the patient will be injured by the surgical probe. Moreover, too strong an electric arc decomposes the tissue and in the case of underwater cutting, as e.g., in urology, the rinsing fluid may even be thermally dissociated. Both processes generate explosive gas mixtures which can lead to dangerous explosions in the patient's body when operating in body cavities.

The power required for cutting and the size and intensity of the resulting electric arc are also influenced by many exterior parameters. The main influencial factors are, e.g., the specific electric conductivity of the tissue being cut, dependent, on the one hand, on the type of tissue and, on the other hand, on the rate at which the tissue is desiccating, the momentary cutting speed, the momentary cutting depth, the shape of the surgical probe, the dimensions of the surgical probe, the specific electric conductivity of a rinsing fluid that might be present: this conductivity can change even during the cutting due to blood flow and electrolytes, the configuration of the operation site, respectively the distribution of high-ohmic and low-ohmic tissue elements there, the momentary current density distribution in the patient's body: this current density distribution can change extremely rapidly and drastically, in particular, if an electric arc is ignited between the surgical probe and the tissue to be cut.

An adjustment of one of the characteristic values of the high frequency surgical generator, which are, e.g.

the high-frequency current delivered to the patient, the high-frequency voltage applied to the patient, the high-frequency power input to the patient, and the no-load voltage set at the generator, can compensate for only some of the influences due to the external parameters. Thus, e.g. an adjustment proposed in DP-A-0285 962 of the output voltage to a constant value largely compensates for the influences: cutting depth and cutting speed. An altered specific electric conductivity of the tissue, e.g. due to desiccation of the tissue requires changing the output voltage, can therefore not be influenced, in particular, by such an adjustment.

The optimum setting of the high-frequency generator is when there is a small electric arc between the surgical probe and the tissue. On the one hand, the electric arc ensures a cutting-friendly dot-shaped transmission of the high-frequency current from the surgical probe to the tissue, but on the other hand does not lead to the described drawbacks of a strong electric arc.

German patent P 25 04 280, describes an apparatus for cutting and/or coagulating human tissue with high-frequency current having a indicator device which shows the size and intensity of the electric arc occurring between the probe and the tissue by means of an electric signal and which contains an adjustment device which regulates the strength of the current of the high-frequency current delivered to the patient and thereby also the high-frequency power input to the patient in such a manner that the size and intensity of the electric arc corresponds to a pre-set value.

Measurements during operations conducted with surgical generators whose output setting is carried out according to this adjustment principle show distinct advantages over operations with generators lacking such controls. Even if the paramenters also influencing the necessary generator setting change drastically, such as electric conductivity of the tissue, the degree at which the tissue is desiccating, cutting speed, cutting depth, shape and dimensions of the surgical probe, etc., one and the same setting of the desired value for the size and intensity of the electric arc can be operated with. As there is hardly any scab formation, the power input to the patient could be decreased in some cases to a third compared to similar operations with a generator without an electric arc adjustment.

Nonetheless, the adjustment has some drawbacks. They can be described if the physical effects connected with cutting at the operation site with a burning electric arc are examined more closely. The electric arc is not dependent solely on the power dosage. A number of other physical effects influence the size and intensity of the electric arc.

First of all, the electric voltage between the surgical probe and the tissue must be sufficiently high that an electric arc can even ignite. This requires, on the one hand, a suitably high no-load voltage of the generator, but also the presence, on the other hand, of a high-ohmic or insulating layer between the surgical probe and the tissue. If the surgical probe is covered with crust, this layer may, under circumstances, be formed by a coat of dried, coagulated blood and adhering remains of tissue. If there is a small gap between the surgical probe and the tissue, air or a only minimally conductive rinsing fluid forms the high-ohmic or insulating layer. If the surgical probe comes into contact with the tissue and it has a clean surface, this high-ohmic or insulating layer is formed by a vapor layer created when the cell fluid vaporizes. The thickness of the resulting vapor layer depends on the electric input power.

The thickness of the high-ohmic or insulating layer then itself influences the electric arc and its effects. The thicker the high-ohmic or insulating layer, the greater the sparking distance of the electric arc and the greater the amount of power is converted into energy at the arcing point of the electric arc. This causes some of the described drawbacks
} when a strong electric arc occurs. As the sparking distance of the electric arc increases, the interrelationship between the high-frequency current in the electric arc and the high-frequency voltage at the electric arc becomes more and more non-linear. This increases the non-linear signals, primarily harmonious with the momentary generator frequency, caused by the high-frequency current and high-frequency voltage in the electric arc. These are, on the one hand, the harmonic 2nd, 3rd, 4th, and higher order, whose frequencies are the twofold, threefold, fourfold, . . . of the momentary frequency of the output signal and it is the harmonic 0 (zero) order which describes the rectifier effect of the electric arc. This rectifier component created in the electric arc is responsible for the nerve and muscle stimulation.

The thickness of the vapor layer as a thermal effect does not immediately follow the momentary power input. Thus the adjustment system has a dead time. This is especially noticeable when starting to cut. Between the point of switching on the generator and the point when the electric arc first ignites, there is an not to be neglected interval; it sometimes takes several seconds until cutting actually commences. It is a known fact in adjustment technology that adjustment systems which contain dead times are very difficult to stabilize.

Moreover, the electric arc does not burn evenly the whole time on the surface of the surgical probe. The electric arc is, if the voltage is sufficiently high, ignited there where the vapor layer is the thinnest. The high concentration of energy generated by the electric arc at the arcing point of the high-frequency current vaporizes the cell fluid there, the arcing point then quickly becomes the point with the thickest insulating layer. The electric arc then ignites at another point. In this way, the electric arc scans the entire surface of the surgical probe and ultimately vaporizes the cell fluid along its entire surface. The site and the sparking distance of the electric arc is so random that the burning of the electric arc must be considered a stochastic process. This effects the spectrum of high-frequency current and high-frequency voltage. Thus, e.g. the spectral ranges created by the electric arc are not of constant amplitude, the speed of change reaching the upper limit which is predetermined by the working frequency. As a result there is, in addition, a broadband noise in the frequency spectrum, used in EP-A0O 219 568 to detect the electric arc.

If such stochastic fluctuations influence the measured values employed for adjustment, the incidental fluctuations have to be compensated by averaging. The measurement of the stochastic processes therefore requires a finite measuring period. This, on the other hand, means that the adjustment cannot occur at any desired rate. Due to this finite period, which passes until there is an unequivocal control value, the electric arcs cannot be adjusted to a constant momentary value. An additional problem in adjusting electric arcs lies in the known physical fact that the non-linear interrelationship between the high-frequency voltage and the high-frequency current in the electric arc has partially negative rises, i.e. it can happen that when raising the momentary voltage, the momentary current decreases and when lowering the momentary voltage the momentary current rises. It is known that such processes can excite oscillations and destabilize adjustments.

DESCRIPTION OF THE INVENTION

The object of the present invention is thus to design the system for cutting biological tissue with high-frequency currents in such a manner that a stable adjustment is obtained despite the afore-described dead times, the required averaging and the threat of destabilization of the adjustment by the physical effects of the electric arc.

Accordingly, in order to indicate the size and intensity of the electric arc, the system is combined with an adjustment of at least one of the characteristic values of the generator. At least one of the characteristic values of the generator is adjusted to a 1st desired value. In this way, the effect of one component of the external parameters on the cutting behavior is eliminated. Preferably, the characteristic value is adjusted to a desired value which influences the external parameter that has the most influence on the cutting process in the type of surgery just being conducted. If the type of tissue and the desiccation state only change slowly, but the cutting depth or cutting speed have to be varied continually, it is advantageous to adjust the output voltage.

In setting the high-frequency current or the high-frequency power to a 1st desired value, the influence of the specific electric conductivity on the cutting behavior is largely eliminated; in this event the influence of the cutting depth and cutting speed on the cutting behavior remain.

These uninfluenceable effects of external parameters by the respective setting of the characteristic value of the generator are compensated for in that the 1st desired value is not constant but is gained by a comparison of the electric signal of a indicator device for the size and intensity of the electric arc with a 2nd desired value. The gaining of the 1st desired value occurs in an evaluation unit to which, on the one hand, the electric output signal of the indicator device for the size and intensity of the electric arc is transmitted and, on the other hand, to which the 2nd desired value is transmitted. For stable adjustment, it is necessary that the 1st desired value generated in the evaluation unit for the adjustment device changes slower by at least one order of magnitude than the adjustment device which needs time to adjust the characteristic value to the desired value.

Short-term changes of the external parameters are thus regulated by quick operating adjustment of the characteristic value in its effect on the cutting behavior. Averaged over a longer period, the size and intensity of the electric arc are constant and determined by the 2nd desired value.

The 2nd value for the size and intensity of the electric arc are supplied by the desired-value transmitter. In the simplest case, the desired-value transmitter supplies a fixed desired value. Usually the surgeon can influence the 2nd desired value supplied by the desired value transmitter and adapt it to the goal of the operation. Very small 2nd desired values for the size and intensity of the electric arc lead to incisions with minimal necrosis and minimal muscle and nerve stimulation. This setting is selected if, e.g., cutting is in the vicinity of nerve centers and there is a danger that the patient will twitch because these nerves have been stimulated. Such sudden movements by the patient make surgery more difficult and present the risk that the surgeon may cut too deeply and thereby seriously injure the patient.

In surgery in which much tissue is to be removed, e.g., in the case of prostatectomy up to 100 g of prostate tissue, a higher setting of the desired value for the size and intensity of the electric arc permits quick cutting. As at the beginning of this type of surgery, the tissue is removed in several layers, a greater degree of necrosis in the top layers is no problem, because these necrotic sections of tissue will be removed in the course of the operation.

The invented combination of an adjustment device for a characteristic value of the generator component and the indicator device for the size and intensity of the electric arc yields further advantages for the design of the system for cutting biological tissue.

Thus the adjustment of the characteristic value does not have to occur precisely; minor deviations in the adjustment are compensated for over a long period by the readjustment of the 1st desired value.

Moreover, it is not necessary that one of the output signals of the generator such as output voltage, output current, output power, no-load voltage, etc. is immediately utilized as the adjusted characteristic value. But rather, characteristic values occurring within the generator component can be adjusted if they simply have an unequivocal relationship to the output values of the generator. Thus, it suffices, e.g., if during a final high power stage of the generator component, which is set up so that it has little interior resistance and its output voltage, therefore, is almost proportional to the voltage of its direct current supply except for a not very great decline in voltage at this interior resistance, to adjust this direct current voltage. In such a case, the complexity of the circuit for the adjustment device may be substantially reduced.

The combination of the adjustment device for one of the characteristic values with the indicator device for the size and intensity of the electric arc hereto also permits utilizing physical processes for the indicator devices, which are too slow for a direct adjustment for the constant size and intensity of the electric arc. For instance, the printed patent of the German patent DE 25 04 280 describes as a particular advantage of the adjustment of the 3rd and higher harmonic that only this harmonic permits a rapid adjustment. If, due to the adjustment to a constant desired value for the size and intensity of the electric arc, only adjustment deviations and slowly changing processes have to be compensated, the especially easy-to-be-measured 0 (zero) harmonic can be utilized to indicate the size and intensity of the electric arc with adequate success. If, by way of illustration, the indication of the size and intensity of the electric arc are combined via the 0 harmonic with an adjustment device for the output voltage of the generator component, the following working mechanism for the entire system is yielded: for varying cutting speed and cutting depth, the constant adjustment of the output voltage achieves almost constant cutting conditions and constant size and intensity of the electric arc. A readjustment of the output voltage is only necessary if the conductivity of the tissue at the site of the operation changes. This occurs either if the incision leads into a tissue area of a different type of tissue, e.g. from muscle tissue into fatty tissue, or if the operation area desiccates slowly due to constant heating. In this event, if the output voltage is at first constant, the average size and intensity of the electric arc is reduced. As a result, the low-frequency parts and, in particular, also the rectified current decrease. The output signal of the electric arc adjustment becomes smaller, the evaluation unit raises the 1st desired value for the adjustment device until the signal of the indicator device in turn equals the 2nd desired value for the size and intensity of the electric arc.

If a physical effect, which permits quick dectection of the size and intensity of the electric arc, is utilized to indicate the electric arc, as for example the evaluation of the harmonics of a higher order contained in the generator current, the evaluation unit has to restrict the changing speed of its output signal, thus the 1st desired value supplied to the adjustment device, by suitable means in such a manner that the rising speed is at least one order of magnitude smaller than the adjustment speed of the adjustment device.

In an especially favorable design of the present invention, the restriction of the changing speed occurs in that first the momentary deviation of the output signal of the indicator circuit for the size and intensity of the electric arc is compared to the 2nd desired value. A possible circuit realization of this comparison can occur by establishing the difference of the two signals, perferably with a differential amplifier. The thereby formed difference signal will initially still change quickly. If then the temporal average value of the signal is established, this output signal is suited to be transmitted as the 1st desired value to the adjustment device. Circuits for averaging are public knowledge. The simplest realization is an RC low-pass filter with a defined cutting-off frequency of $f_{g1}$.

In another advantageous embodiment of the evaluation unit, a difference signal is also formed from the output signal of the indicator device for the size and intensity of the electric arc and the 2nd desired value for the size and intensity of the electric arc. This output signal is transmitted to a circuit with a temporally integrating function, as e.g. can be realized in a known manner with the aid of a capacitive feedback differential amplifier. In this case, the size and intensity of the electric arc is changed until the output signal of the indicator device for the size and intensity of the electric arc equals the 2nd desired value for the size of the electric arc without any permanent adjustment deviation. A possibly necessary direct current voltage offset for the 1st desired value, transmitted to the adjustment device, sets in automatically due to this design.

Due to averaging or integration, the 1st desired value changes only slowly. Because of the previously described dead times until the ignition of an electric arc, it is usually useful to only raise the output signal of the generator very slowly. If the electric arc occurs then, the 1st desired value is only a little larger than would be optimum in the transient state of the adjustment despite the dead times. The size and intensity of the electric arc is then also almost optimum. The adjustment speed of the 1st desired value for a higher characteristic value of the generator component is in this case at least one order of magnitude smaller than the adjustment speed of the adjustment device. If too high an electric arc occurs in this case, either because the external parameters have changed or because the dead time lasted too long that the 1st desired value transmitted to the adjustment device rose far above the optimum value, the too strongly burning electric arc would then cause the previously described drawbacks. In this event, the evaluation unit is designed in such a manner that the changing speed of the 1st desired value in the direction which means a downward adjustment of the adjusted characteristic value of the generator component is at least one order of magnitude larger than in the case of an upward adjustment.

A special problem in an adjustment which maintains a constant size and intensity of the electric arc is the time passing between activating the generator and the 1st ignition of the arc. At this point, the tissue to be cut is at body temperature. Now the tissue must first be heated to the boiling point of the cell fluid and sufficient cell fluid must vaporize until the surgical probe and the tissue are completely isolated from one another, not until then can the electric arc ignite. Measurements show that in this case several seconds can pass between activating the generator and igniting the electric arc, especially if the surgical probe is pressed strongly against the tissue when the generator is activated. In this event, the 1st desired value for the adjustment device for adjusting one of the characteristic values of the generator rises steadily during the entire time that the electric arc has not ignited. Without any special measure, a much too large an electric arc burns once the electric arc has ignited. This disadvantage can be avoided if, due to a suited circuit, the 1st desired value cannot rise above a preset limit. Thus, measurements show that, e.g., in dentistry no voltages with an effective value higher than 250 V are needed if the current required for the surgery is returned low-ohmically to the generator. In this case, it is advantageous to adjust the output voltage of the generator as the characteristic value to a constant value but not to permit higher desired values for the adjustment device than are suited for an output voltage of 250 V.

Frequently a bottom limit suited for the application can also be given as the characteristic value of the generator which is adjusted by the adjustment unit to the 1st desired value. Thus values of at least 150 V are required for the amplitude of the voltage applied to the tissue in order to be able to ignite an electric arc at all. In this case, it is advantageous if the desired value for the adjustment device is restricted in such a manner that the limit of the characteristic value suited for the application is not undercut and, of course, the suited top value is not exceeded.

In this event, the required adjustment range for the adjustment of the characteristic value of the generator is restricted permitting achieving higher adjustment speeds and greater adjustment stability.

In another advantageous embodiment of the present invention, the problem of, at times, long delays between activating the generator and igniting the electric arc is avoided by extending the evaluation unit by a circuit component which recognizes whether or not an electric arc has ignited. In its simplest form, this circuit component consists of a comparator which indicates whether the output signal of the indicator device for the size and intensity of the electric arc differs from zero. If the output signal of the indicator device is zero, there is no electric arc. In this case, a fixed desired value is passed on as the 1st desired value for the adjustment device. The 1st desired value is not formed from the comparison of the 2nd desired value with the output signal of the indicator device for the size and intensity of the electric arc until the electric arc has ignited. Naturally, in practical realization, the circuit will be designed in such a manner that averaging or integration circuits do not run into a limit during the time when there is no electric arc. The transient effect of the adjustment would otherwise be needlessly slowed down.

During some surgery, the surgeon already activates the generator some time prior to touching the tissue with the surgical probe. This is especially the case if he only has to remove a small amount of tissue yet has to be particularly careful. In this event, the time between the activation of the generator and the occurance of the electric arc is extended further. The state that the surgical probe has not yet touched the tissue can be determined by monitoring the impedance Z occurring between the surgical probe and the tissue. In another advantageous embodiment, the system for cutting biological tissue is, therefore, supplemented with a circuit for determining the momentary impedance and its output signal is also transmitted to the evaluation device. In connection with the output signal of the indicator device for the size and intensity of the electric arc, the 1st desired value can then be adapted better to the events of the operation.

In an especially advantageous embodiment of the present invention, the 1st desired value for the adjustment device is set to a preset low value as long as a high-ohmic impedance Z indicates that the surgical probe has not touched the tissue. The characteristic value of the generator is not set to the greater value prescribed by the evaluation unit until the impedance Z undercuts a preset limit Zu. The limit Zu depends on the application of the system. If the described system is part of a high-frequency surgical generator for dentistry, the measurements of the inventors show that if the generator frequency is 350 kHz and there is no tissue contact, the load impedance of the high-frequency generator in the case of a surgical system with an applied by-pass electrode is more than 20 kΩ and distinctly less if the tissue is contacted. In this case, it is useful to select an impedance value of Zu=20 kΩ as a threshold value.

The indicator device for the load impedance does not necessarily have to pass on an analogue value to the evaluation unit. The decision whether the surgical probe has touched the tissue or not can already be made in the indicator device for determining the load impedance. In this event, forming the ratio of the generator voltage U divided by the generator current I(Z=U/I) otherwise needed for detemining the impedance is obviated. It suffices to give the comparator a value $v_1*I$ which is proportional to the generator current I and a value $v_2*U$ which is proportional to the generator voltage. The output signal of the comparator will change its switch state exactly when $v_1*I$ equals $v_2*U$ ($v_1*I=v_2*U$). Thus the limit for switching Zu is given by $Zu=v_2/v_1$. The factors $v_1$ and $v_2$ can easily be set with state-of-the-art processes, e.g. by means of voltage-divider circuits. In that event, the output signal of the comparator has only the two switching states which show whether the momentary load impedance Z of the system for cutting biological tissue is greater or smaller than Zu. This signal can then be transmitted to the evaluation unit as the output signal of the indicator device for the load impedance. There it can serve without any or only little further processing as a switching signal from a given low value to the variable value determined from the indicator device for the size of the electric arc as the 1st desired value for the adjustment device.

All state-of-the-art analogue operating circuits having the properties defined in the claims hereto may be utilized for the practical construction of the evaluation unit. As the 1st desired value which is transmitted to the adjustment device for a characteristic value of the high-frequency generator component from the evaluation unit only needs to change slowly, the evaluation unit can also be realized by digital circuit elements in an especially advantageous embodiment. Some new high-frequency surgical generators on the market already contain microprocessors. In this case, the overall system can be particulary easily adapted to the different surgical purposes. It suffices to change the program of the microprocessor in order to obtain different characteristic values or different limits.

BRIEF DESCRIPTION OF THE DRAWINGS

The present invention is made more apparent in the following, by way of example, without the intention of limiting the scope or spirit of the overall inventive idea, using preferred embodiments with reference to the accompanying drawing to which, moreover, is expressly referred for the disclosure of any inventive details not explained more closely herein. Shown are in.

DESCRIPTION OF A PREFERRED EMBODIMENT

Figure 1:
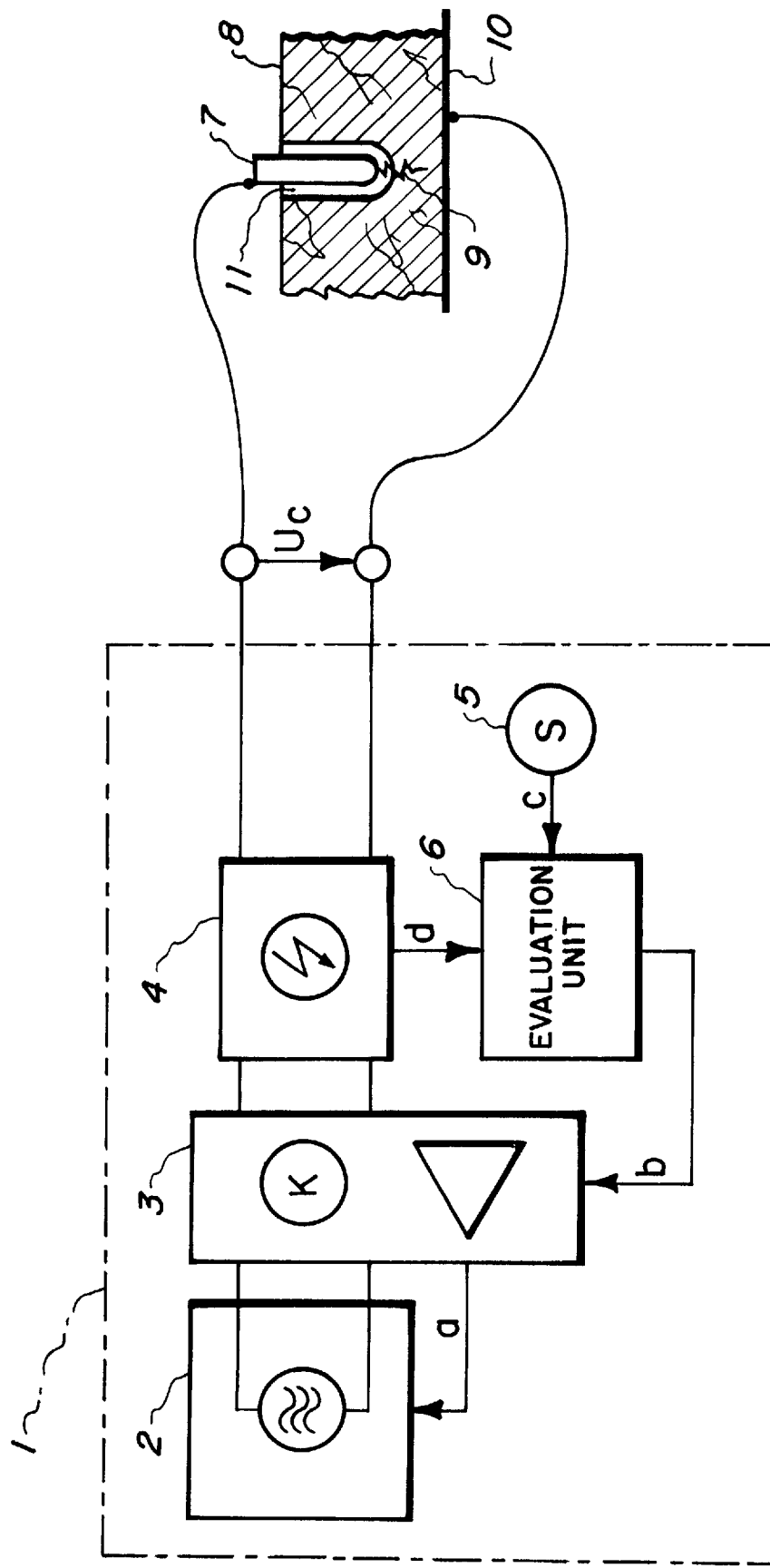
FIG. 1 A basic circuit diagram of the system for cutting biological tissue.

FIG. 1 shows a basic circuit diagram of the system for cutting biological tissue (1) in conjunction with the most frequently used mode of tissue-to-system contacting. One clamp of the system is conductively connected to the surgical probe (7). The surgical probe is often also referred to as active electrode or cutting electrode. The second clamp is usually conductively connected to a second, large-surface electrode (10), which is usually disposed away from the operation site. This second electrode is often referred to as by-pass electrode, neutral electrode or passive electrode. Between the surgical probe (7) and the second electrode is the biological tissue to be cut (8). During the incision, a high-ohmic or insulating layer (11), which is penetrated by an electric arc (9), forms between the surgical probe (7) and the tissue (8). The system for cutting biological tissue consists of a generator component (2) which generates the high-frequency power needed for cutting. Required for the system for cutting biological tissue is a generator component (2) whose output power can be changed by an electronic signal (a). It is not of significance for the present invention which output values of the generator component such as output voltage, output current, output power, no-load voltage is primarily influenced by signal a. All these values are interconnected via the characteristic values of the generator and the impedance fixed by the external circuit.

As further component the system for cutting biological tissue has a device for adjusting at least one of the characteristic values of the generator. In this system, signal (b) represents the 1st desired value to which the characteristic value (K) is adjusted. In the drawing, the device for adjusting the characteristic value is drawn in such a manner that a value (K) which can be detected at the output of the generator component is adjusted. Only a value occurring in the generator component can also be adjusted instead as the characteristic value (K) if it has an equivocal relationship to the output value of the generator component. The 1st desired value (b) occurring in the system for cutting biological tissue is not a set, fixed value, but rather is set by the following described components of the overall system. First there is an indicator device (4) which indicates the size and intensity of an electric arc (9) burning between the surgical probe (7) and the tissue (8) by an electric signal (d) All hitherto state-of-the-art circuits for detecting an electric arc with an electric signal can be used as indicator units, thus in particular all the methods described in the German patent 2504280. The output signal (d) of the indicator device (4) for the size and intensity the electric arc is transmitted to an evaluation unit (6) which forms the 1st desired value (b) for the device for adjusting at least one of the characteristic values of the generator component from the output signal (d) and a desired value c given by a desired-value transmitter (5). It is important for the functioning of the overall system that the 1st desired value (b) changes by at least one order of magnitude slower than the adjustment device for adjusting the required characteristic value requires. Possible embodiments of the evaluation unit (6) are described in the respective description and are made more apparent in the following figures.

Figure 2:
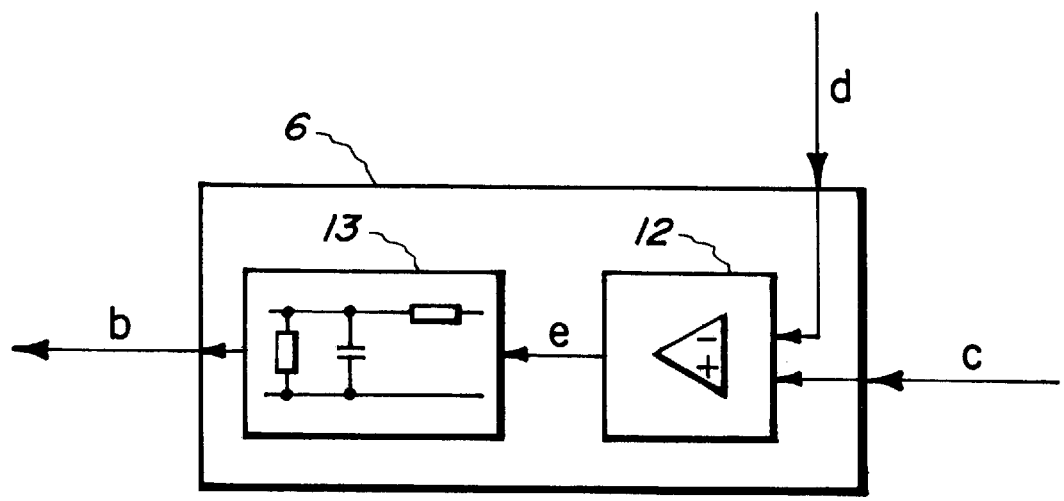
FIG. 2 A basic circuit diagram of an embodiment of the evaluation unit with establishing the difference and averaging, FIG. 3 A basic circuit diagram of an embodiment of the evaluation unit with establishing the difference and integration.

FIG. 2 shows a diagrammatic view of an advantageous embodiment of the evaluation unit (6). The difference signal e is formed from the input signals (d), (c) of the evaluation unit (6) by a difference establishing circuit (12). There are many possibilities familiar to those versed in the art for the realization of the circuit, one of them is the depicted circuit having an operational amplifier. Subsequently, the average value of the difference signal (e) is formed by the circuit (13). The simplest form of linear averaging can occur as described by an RC-low pass filter. Other circuits with low-pass functions are just as suited to solving this object, in particular also active low passes. In their case, the generally also needed addition of an offset value to the output signal is especially easy to solve. Averaging is, however, not restricted to the linear average value as low passes form. Particularly advantageous can be forming the root mean square of the difference signal. In this case, however, the complexity of the circuit increases considerably.

Figure 3:
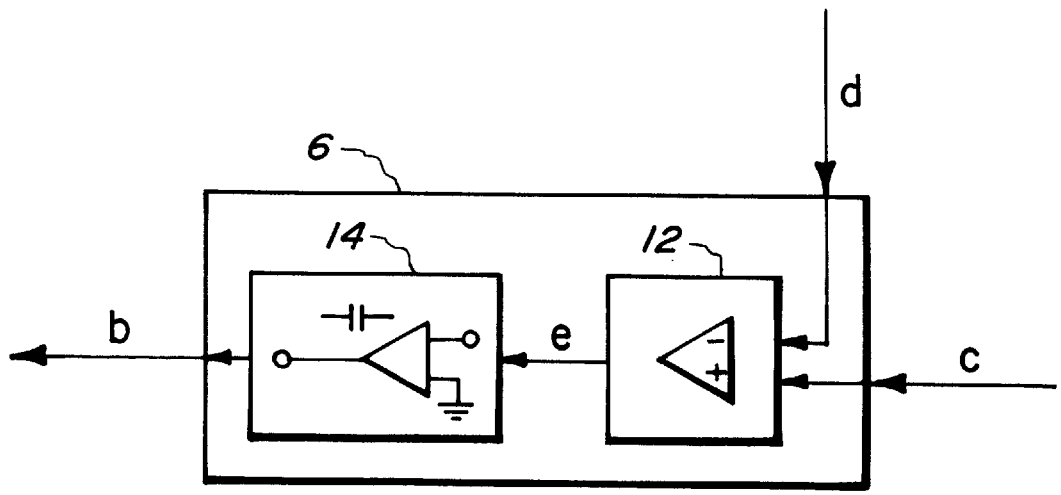

FIG. 3 shows a diagrammatic view of another advantageous embodiment of the evaluation unit (6). Like in FIG. 2, a difference signal e is formed from the input signals (d), (c) of the evaluation unit (6) by a subtraction circuit (12). This is followed by a circuit with an integrating effect (14) like those, e.g., that can be realized with the aid of a capacitive regenerative operational amplifier. The special advantages of this circuit arrangement is that the size and intensity of the electric arc can be adjusted to the 2nd desired value (c) without any permanent adjustment deviation even if the 1st desired value (b) has to be provided with an offset value which changes with the time or with the surgical temperature.

Figure 4A:
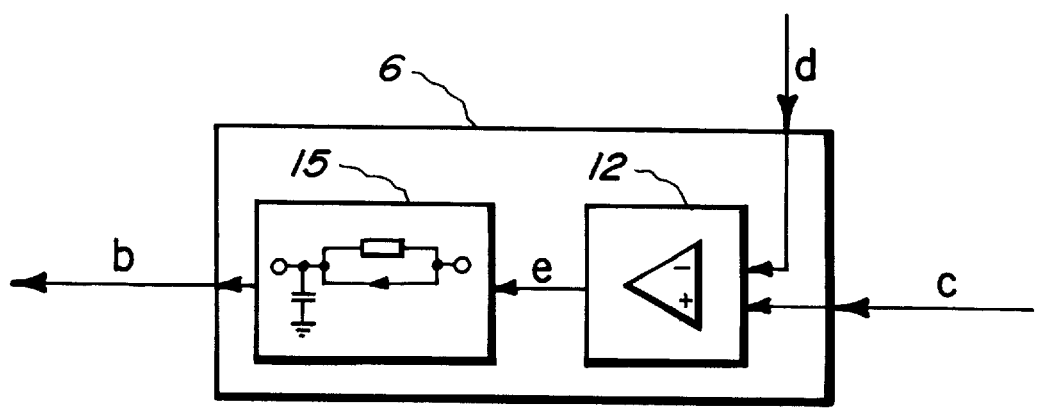
FIGS. 4(a), 4(b) and 4(c) are a basic circuit diagram of an embodiment of the evaluation device with different time constants for the adjustment in upward direction, respectively downward direction, with diagrams of the time courses of the adjustment signals, FIG. 5 A basic circuit diagram of an embodiment of the evaluation unit with the desired value for the adjustment device restricted to a maximum limit, FIG. 6 A basic circuit diagram of an embodiment of the evaluation unit with the desired value for the adjustment device restricted to a maximum top limit and a minimum bottom limit, FIG. 7 A basic circuit diagram of an embodiment of the evaluation unit, in which the desired value for the adjustment device is switched to a preset, fixed value B1 as long as no electric arc has been identified, FIG. 8 A basic circuit diagram of the system for cutting biological tissue, FIG. 9 A basic circuit diagram of an embodiment of the evaluation unit, in which the desired value for the adjustment device is switched to a preset, fixed value B2 as long as the load impedance Z is smaller than a preset limit Zu.

FIG. 4(a) shows a diagrammatic view of another advantageous embodiment of the evaluation unit (6). Like in FIGS. 2 and 3, a difference signal e is formed from the input signals (d), (c) of the evaluation unit (6) by a difference establishing circuit (12). This is followed by a circuit having a low-pass behavior (15) and/or with an integrating effect. Contrary to the circuits described in FIGS. 2 and 3, this circuit has different time constants depending on whether the signal (d) indicating the size and intensity of the electric arc is larger or smaller than the 2nd desired value (c). The simplest possibility of realizing such different time constants is to couple the storing element of the circuit for averaging or the integration circuit to the previous circuit via different resistances. Switching can occur, as shown diagrammatically in FIG. 4 by a diode (D1). The same function could, however, also be obtained via controlled switches.

Figure 4B:
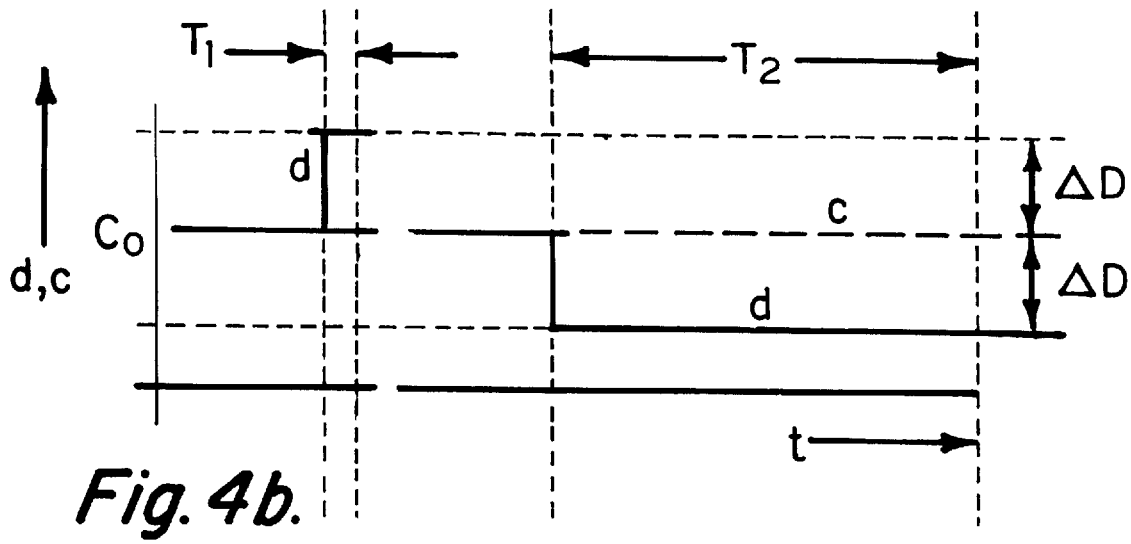
Figure 4C:
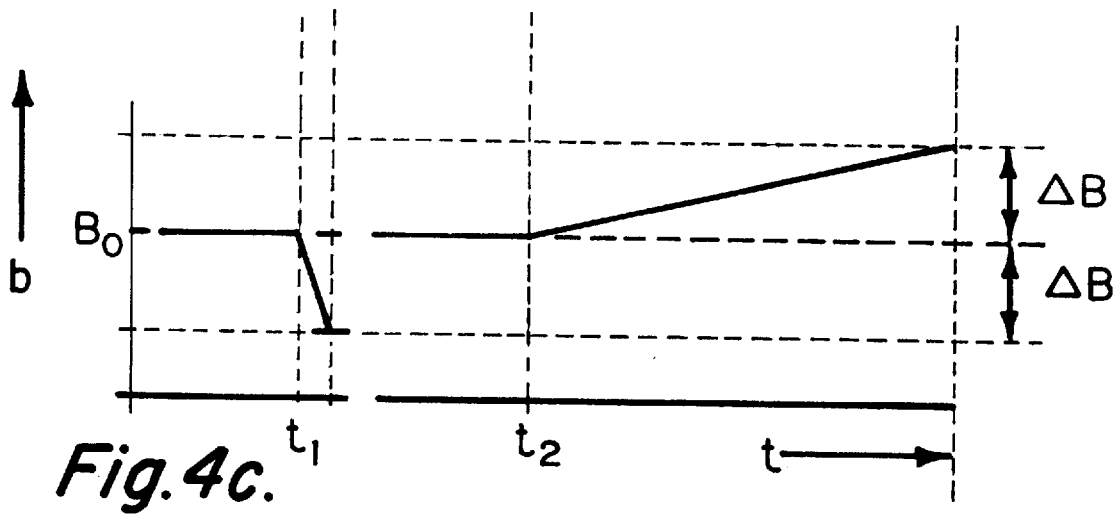

The intention of the time diagram in FIGS. 4(b) and 4(c) is to make the function of the circuit more apparent. First the input signals (c) and (d) of the evaluation unit (6) are entered in the diagram. The desired 2nd value (c) indicating the desired size and intensity of the electric arc should be constant the entire time ($C_0$) (interrupted line). For signal 2 describing the actual size and intensity of the electric arc at the time $t_1$ the size and intensity of the electric arc has suddenly become larger, by the value D. In response to this, the output signal b of the evaluation unit representing the 1st desired value for the following adjustment device (3) lowers. Due to the low-pass behavior of the averaging or integrating circuit (15), it takes a finite time span of $T_1$ until the output signal b reaches a determined deviation B from the previoulsy assumed value $B_0$. The next thing drawn in the diagram at the time $t_2$ is a deviation D of the signal d from the value $c=C_0$ in the direction indicating the decreased size of the electric arc. Now it takes a considerably longer time span $T_2$ until the signal b reaches the same deviation B of the value $B_0$. An inventive element is that the circuit (15) is designed in such a manner that time span $T_2$ is substantially larger than time span $T_1$, thus it can be said $T_2 >> T_1$. The drawn Time course of signals c, d and b are only intended to illustrate the basic behavior of the circuit. They cannot be measured in the drawn manner in a closed adjustment loop in the actually realized circuit. Any change in the signal b immediately results in a change in the adjusted characteristic value of the generator component and therefore also in a change in the size and intensity of the electric arc and a change in signal d. A temporal constant deviation in signal d by the value D is thus possible in a closed adjustment loop. The signals can, however, be measured in a similar manner if the adjustment loop, as is common in basic tests, be opened at any point.

Figure 5:
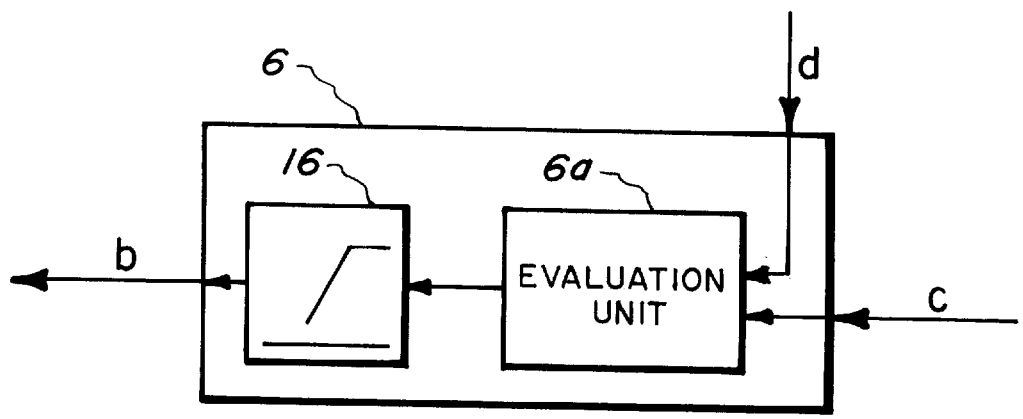

FIG. 5 shows another advantageous embodiment of the evaluation unit. The circuit block 6a is an embodiment of the evaluation unit 6 previously completely described in FIGS. 1–4. Before the output signal is transmitted to the adjustment device as the 1st desired value (b), there is now a limit circuit 16 which prevents signal b from rising above the limit $B_{max}$.

Figure 6:
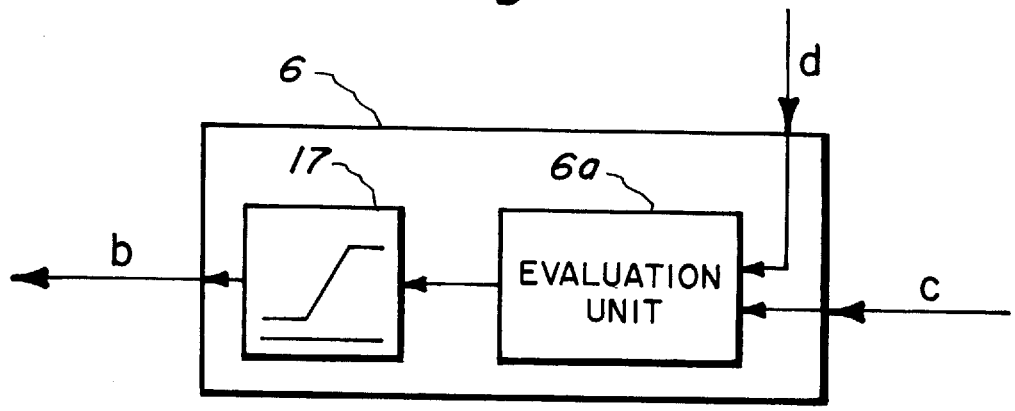

FIG. 6 shows another advantageous embodiment of the evaluation device. The circuit block 6a is an embodiment of the evaluation device 6 previously completely described in FIGS. 1–4. Before the output signal is transmitted to the adjustment device as the 1st desired value (b), there is now a limit circuit 17 which prevents signal b from rising above the top limit $B_{max}$ and dropping below the bottom limit $B_{min}$.

Figure 7:
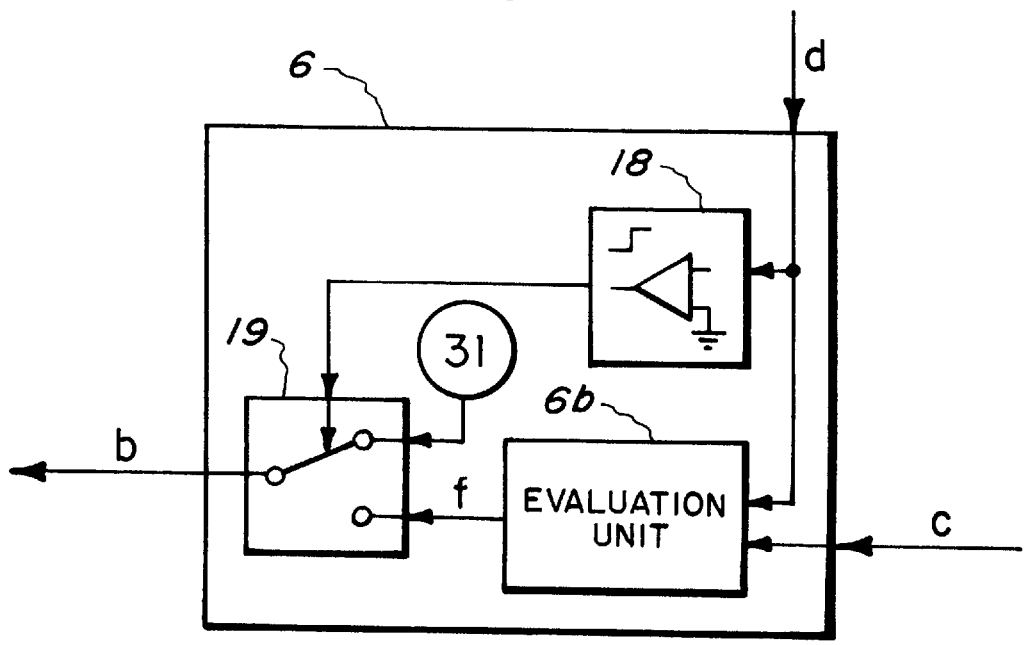

FIG. 7 shows another advantageous embodiment of the evaluation device. The circuit block 6b is an embodiment of the evaluation device 6 previously completely described in FIGS. 1–6. The output signal of the circuit component (6b) is only transmitted as the 1st desired value (b) to the adjustment device if there is an electric arc. In the times in which there is no electric arc, the preset value B1 is applied for the signal b by the change-over switch (19). The decision concerning the change-over occurs in the circuit component (18) which, in the simplest embodiment, consists of a comparator which determines whether the size and intensity of the electric arc indicated by signal d differs from zero.

Figure 8:
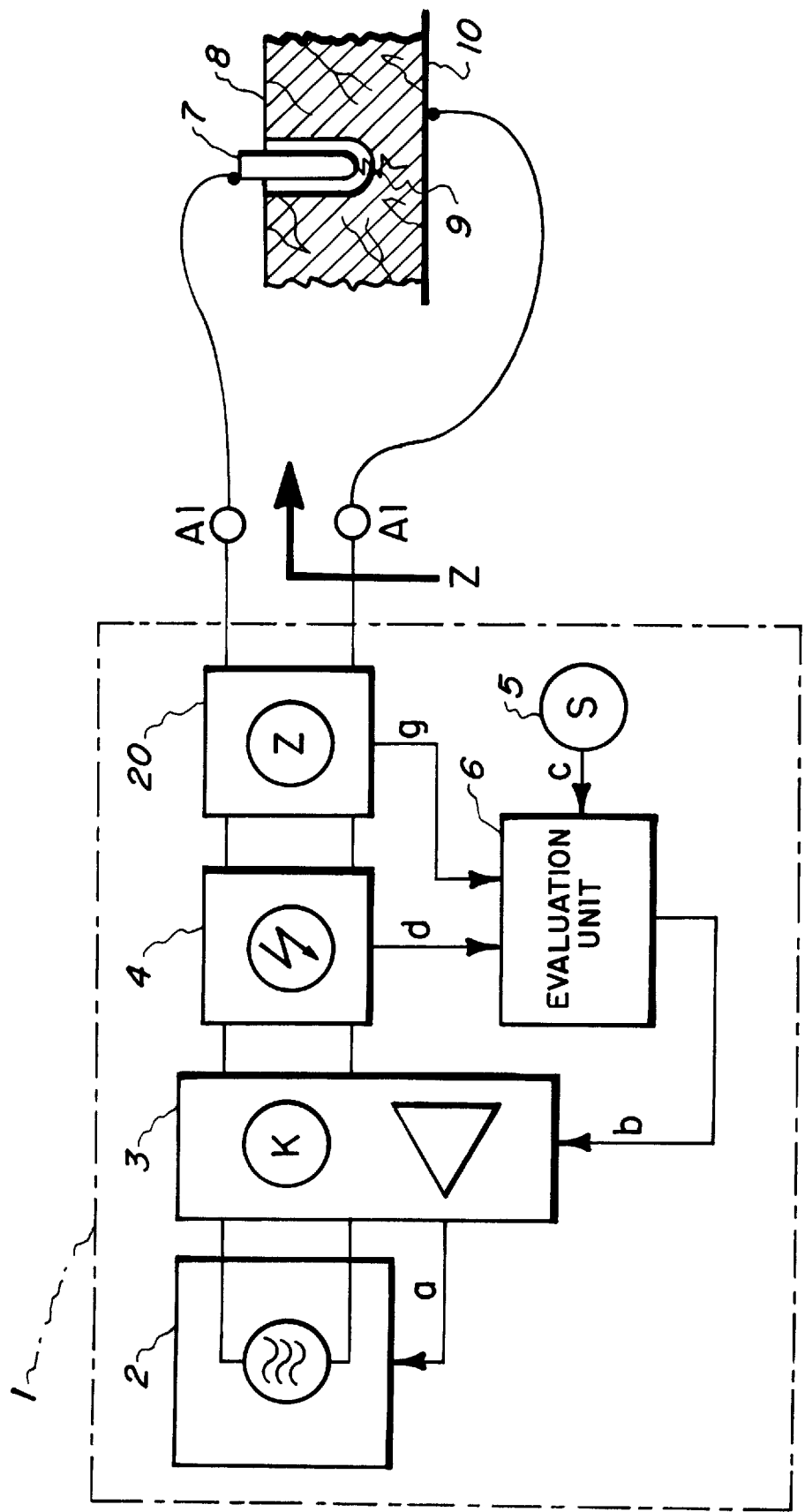

FIG. 8 describes another advantageous embodiment of the present invention. FIG. 8 shows in another diagrammatic view the entire system for cutting biological tissue. In addition to the function units shown in FIG. 1, there is the indicator device (20) for the impedance Z with its output signal g which is also transmitted to the evaluation unit (6). The impedance Z is the load impedance which occurs at the output clamps (A1, A1') of the overall system through connection to the biological tissue. By including the impedance Z in the forming of the 1st desired value (b) for the adjustment device, more attention can be paid to the momentary surgical conditions at the site of the surgery.

Figure 9:
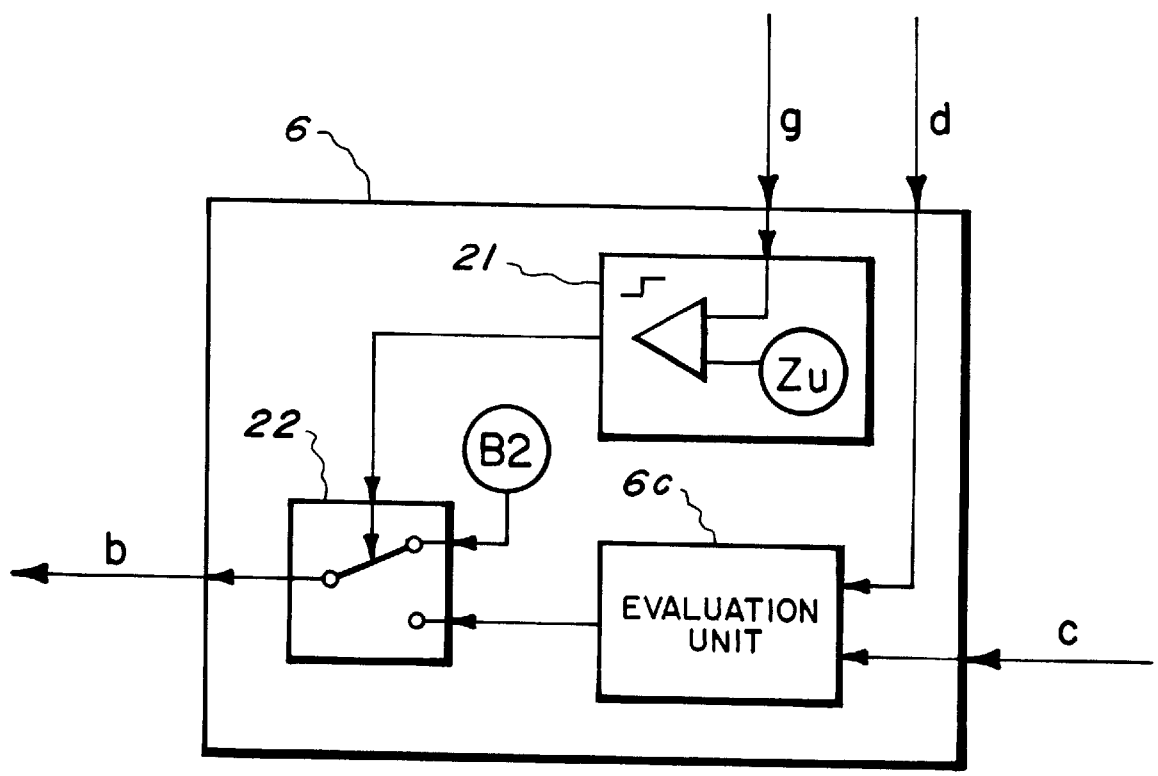

FIG. 9 shows a simple but especially advantageous embodiment of the evaluation device (6) which, in addition, includes the value of the momentary impedance Z in its assessment. Block 6c is one of the embodiments of the evaluation device 6 described in the FIGS. 1 to 7. In addition, there is now a comparison circuit provided which determines whether the momentary impedance is larger or smaller than the preset value of Zu. If Z>Zu, the surgical probe is not in contact with the tissue. In this case, a diminished value B2 is transmitted as the 1st desired value b to the adjustment device of the characteristic value of the generator component by the change-over switch (22).

What is claimed is:

1. A system for controlling the operation of a high frequency biological tissue cutting device comprising;
   an amplitude adjustable high frequency generator (2) for delivering a high frequency voltage to a cutting probe (7);
   at least one adjustment device (3) for adjusting at least one of several characteristic quantities (K) of voltage, current, impedance and frequency of said high frequency generator;
   an indicator device (4) connected to said adjustment device (3) providing an output signal representing the actual size and intensity of an electric arc at said cutting probe (7);
   a desired value transmitter (5) for providing a desired value representing a desired size and intensity of said electric arc;
   an evaluation unit (6) receiving outputs from said indicator device (4) indicating values representing an actual size and intensity of said electric arc and said desired value transmitter (5) representing a desired size and intensity of said electric arc and producing an output signal to said adjustment device;
   means for controlling the output signal from said evaluation unit (6) so that an upward adjustment is substantially slower than a downward adjustment;
   whereby said control system continuously adjusts the output of said high frequency generator according to the tissue conditions of said cutting probe.

2. The control system according to claim 1 in which said evaluation unit includes; a subtraction circuit for providing an output which is a difference signal from said indicator output and said desired value output; and an averaging circuit which averages said difference signal temporally.

3. The control system according to claim 1 in which said evaluation unit includes; a subtraction circuit for providing an output which is a difference signal from said indicator output and said desired value output; and an integration circuit for integrating said difference signal temporally.

4. The control system according to claim 3 in which said evaluation unit includes a limiting circuit (16) which limits said output signal to a maximum.

5. The control system according to claim 4 in which said limiting circuit also limits said output signal to a predetermined minimum.

6. The control system according to claim 5 in which said evaluation unit includes a means providing a preset output signal until an arc is detected and switch means for switching to a controlled output signal when an arc is detected.

7. The control system according to claim 6 including means for measuring momentary impedance of said system for cutting tissue; said momentary impedance being transmitted to said evaluation unit.

8. The control system according to claim 7 in which said evaluation unit includes means to provide a low value output as long as said momentary impedance is above a preselected threshold value.

9. The control system according to claim 8 in which said momentary impedance measuring means has two switching states comprising; first switching state means for when said momentary impedance (Z) is smaller than said threshold value (Zu) and a second switching state means for when said momentary impedance (Z) is above said threshold value (Zu).

10. The control system according to claim 2 in which said evaluation circuit includes means reducing said output signal to said adjustment device substantially faster for an electric arc that is too large, than it raises said signal for an electric arc that is too small.

11. The control system according to claim 10 in which said evaluation unit includes a limiting circuit (16) which limits said output signal to a maximum.

12. The control system according to claim 11 in which said limiting circuit also limits said output signal to a predetermined minimum.

13. The control system according to claim 12 in which said evaluation unit includes means providing a preset output signal until an arc is detected and switch means for switching to a controlled output signal when an arc is detected.

14. The control system according to claim 13 including means for measuring momentary impedance of said system for cutting tissue; said momentary impedance being transmitted to said evaluation unit.

15. The control system according to claim 14 in which said evaluation unit includes means providing a low value output as long as said momentary impedance is above a preselected threshold value.

16. The control system according to claim 15 in which said momentary impedance measuring means has two switching states comprising first switching state ns for when said momentary impedance (Z) is smaller than said threshold value (Zu) and a second switching state means for when said momentary impedance (Z) is above said threshold value (Zu).

* * * * *